United States Patent [19]

Rudin et al.

[11] 4,403,338

[45] Sep. 6, 1983

[54] PROCESS AND APPARATUS FOR SCATTER REDUCTION IN RADIOGRAPHY

[76] Inventors: Stephen Rudin, 133 Old Farm Cir., Williamsville, N.Y. 14221; Daniel R. Bednarek, 24 Woodell Ave., Cheektowaga, N.Y. 14211; Roland Wong, 268 Windermere Blvd., Amherst, N.Y. 14226

[21] Appl. No.: 206,698

[22] Filed: Nov. 14, 1980

[51] Int. Cl.³ .............................................. G03B 41/16
[52] U.S. Cl. ..................................... 378/146; 378/160
[58] Field of Search ................ 250/505, 508, 509, 514

[56] References Cited

U.S. PATENT DOCUMENTS

| | | | |
|---|---|---|---|
| 2,453,163 | 11/1948 | Shurcliff | 250/509 |
| 3,684,885 | 8/1972 | Cook | 250/509 |
| 4,031,401 | 6/1977 | Jacob | 250/509 |
| 4,315,146 | 2/1982 | Ruden | 250/509 |

Primary Examiner—Craig E. Church
Attorney, Agent, or Firm—Michael L. Dunn

[57] ABSTRACT

An apparatus and method for reducing detection of radiation scatter from an object through which radiation passes from a source to a radiation detection means having a detecting surface. The apparatus comprises at least one radiation shield having front and rear curvilinear shield surfaces. Each of the curvilinear shield surfaces, with projected continuations thereof, is circularly symmetrical about a central axis. Each shield surface, or its projected continuation, intersects the axis at an apex. The front and rear surfaces share the same central axis. The apparatus further includes a means for mounting the shield, between the object and the detecting surface, to make it movable about the central axis and to align the central axis on a straight line from the source to the apexes of the surfaces so that all radiation passing from the source through the object must pass once through the shield, when the shield is in motion about the axis, before the radiation strikes the detecting surface. The apparatus further includes a means for moving the shield about the central axis. The shield is provided with a series of openings which allow radiation in a straight line from the source toward the detecting surface to pass through the openings to strike the detecting surface.

The process for reducing detection of radiation scatter comprises; interposing at least one shield, as previously described, between the object and the detecting surface; aligning the shield so that the central axis of the shield is on a straight line from the source to the apexes of the surfaces and so that all radiation passing from the source through the object must pass once through the shield, when the shield is in motion about the axis, before the radiation strikes the detecting surface; and moving the shield about the central axis.

20 Claims, 9 Drawing Figures

PROCESS AND APPARATUS FOR SCATTER REDUCTION IN RADIOGRAPHY

BACKGROUND OF THE INVENTION (a) Field of the Invention

This invention relates to diagnostic radiology and in particular relates to the use of high energy radiation to form images of internal structures upon a sensing means such as a luminescent, e.g., fluorescent screen. The invention more particularly relates to a method and apparatus for reducing detection of radiation scatter in forming such images.

(b) History of the Prior Art

Originally, X-ray photographs were taken simply by directing X-rays from a source, e.g., an original roentgen ray tube, through an object, such as an anatomical structure, to a detector such as an X-ray film. This initial historical arrangement did not include additional devices to reduce hazards to a patient or to enhance the quality of the detected X-ray image.

Later X-ray devices not only used improved X-ray tubes, such as tubes which in conjunction with other components could control intensity and wave length of X-rays, but also incorporated filters for eliminating radiation outside of the useful X-ray range and included means for enhancing the contrast of the image by eliminating at least a portion of radiation scatter from the object, such as a patient, to the detector. Such scatter often results when high energy radiation interacts with atomic fields or particles. Scattered radiation is usually emitted in a direction different than the direction of the incoming primary radiation. The scattered radiation thus causes exposure of the detector to radiation at all locations thus reducing contrast of the detected image with the background.

The most usual method for reducing scatter historically has been and remains radiographic grids which consist of a series of lead foil strips separated by X-ray partially transparent spacers. The lead foil acts to intercept secondary or scattered radiation which approaches the detector at an inappropriate angle. Such grids have, however, certain undesirable characteristics. For example, contrast is still not as high as desired since all scatter is still not eliminated, primary radiation is absorbed by interspaces and grid lines become apparent on the X-ray image since the lead strips absorb primary radiation from the radiation source.

Attempts have been made to eliminate the appearance of the grid pattern in the X-ray image by moving the grid in a direction essentially perpendicular to radiation passing from the source to the detector; however, such a moving grid did nothing to increase contrast. In addition, since the angle of radiation from a fixed source to a point on a planar grid changes as the grid moves, an appropriate fixed angle between grid members to allow maximum passage of primary radiation between the members is not possible. There has also been an attempt to utilize linearly moving aligned slit devices to increase contrast. The devices have to be moved at a uniform speed and have to reach that speed before the X-ray is taken. This requires that the X-ray be taken in a precisely timed relationship to slit motion. Furthermore, vibration within the system cannot be tolerated and uniform X-ray output must be maintained during exposure to prevent unwanted artifact patterns on the detector. The moving slit system is also subject to the problem of radiation angle change as the slits move thus requiring complex mechanical devices to change the angle of the slits as they move.

Attempts have been made to use rotating planar disks to reduce the detection of secondary radiation. See French Pat. No. 521,746 (1921); Rudin et al., "Rotating Aperature Devices in Conventional Tomography," Proceedings of the Society of Photo-Optical Instrumentation Engineers (SPIE) Vol. 233, (1980); Rudin, "Fore-and-Aft Rotating Aperature Wheel (RAW) Device for Improving Radiographic Contrast," SPIE, Vol. 173, (1979); and Sorenson et al., "Rotating Disc Device for Slit Radiography of the Chest," Radiology, Vol. 134, (January 1980).

All of these disk devices have major deficiencies. In particular unless the disk or disks rotate on the same perpendicular axis upon which the radiation source is located, the problem of radiation angle change as the holes or slits move is not alleviated and if the disks do rotate on the same perpendicular axis upon which the radiation source is located, X-rays may not be used perpendicularly to the plane of the disk since perpendicular rays pass through the central axis which contains the means for supporting the disk. The inability to use rays perpendicular to the disk means that the disks may not be parallel to the object being X-rayed unless distorted oblique X-ray views are desired. When a disk is placed at an angle to the object, large undesirable distances between the object and detector are required.

Devices using concentric rotating cylinders have also been described. See e.g., French Pat. No. 521,746 which describes concentric moving bands and Rudin, "Rotating Aperature Devices in Conventional Tomography," SPIE, Vol. 233, (1980), which describes cylinders for use in conjunction with Computed Tomography (CT) devices. Concentric rotating cylindrical devices are undesirably large since the object must be placed within any cylinders having walls between the object and detector

BRIEF DESCRIPTION OF THE INVENTION

In accordance with the invention there is provided an apparatus and method for reducing detection of radiation scatter from an object through which high energy radiation passes within a flux pyramid from a source to a radiation detection means having a detecting surface.

The apparatus comprises at least one radiation shield having front and rear curvilinear shield surfaces. Each of the curvilinear shield surfaces, with projected continuations thereof, is circularly symmetrical about a central axis. Each shield surface, or its projected continuation, intersects the axis at at least one and not more than two apexes. The front and rear curvilinear surfaces share the same central axis. The shield is sufficiently dense and thick between the front and rear surfaces to absorb essentially all radiation from the source which strikes the shield. The front surface faces the source and faces the central axis and at least a portion of the rear surface faces the detecting surface.

The apparatus further includes a means for mounting the shield between the object and the detecting surface, to make it movable about the central axis and to align the central axis on a straight line from the source to the apexes of the surfaces so that all radiation passing from the source through the object must pass once through the shield when the shield is in motion about the axis before the radiation strikes the detecting surface. The portion of a shield which is at least sometimes located so that radiation from the source to the detecting surface must pass through that portion is the utilized portion of the shield. The front and rear surfaces define the utilized portion of the shield. The apparatus further includes a means for moving the shield about the central axis.

The shield is provided with a series of openings, narrower than the object, passing through the shield from the front to the rear surface. The openings allow radiation to pass through the shield from the source to the detecting surface. The openings are in shapes and positions such that at least a portion of the radiation in a straight line from the source toward the detecting surface passes through the openings in the shield to strike the detecting surface.

The process for reducing detection of radiation scatter essentially involves utilizing the apparatus of the invention wherein radiation shields, as previously described, are interposed between the object and the detecting surface and aligned so that the central axis of the shield is on a straight line from the source to the apexes of the surfaces and so that all radiation passing from the source through the object must pass once through the shield, when the shield is in motion about the axis, before the radiation strikes the detecting surface. The process further comprises moving the shield about the central axis.

The apparatus and process of the invention permits essentially all radiation from a point source on the axis to strike the front surface of the shield in planes perpendicular to the front surface. Since radiation strikes the surface in planes perpendicular to the surface, much less primary radiation is lost by striking side walls of holes through the shield, when the side walls of the holes are perpendicular or essentially perpendicular to the front surface. Side walls of the holes, as opposed to end walls of the holes, are defined by straight lines from the nearest apex. "Essentially perpendicular," as used in this context, means varying from perpendicular by not more than ten degrees. Furthermore, the shield, when sufficiently thick or when used in conjunction with other aligned shields having a similar configuration, permits the passage of primary radiation while greatly reducing the passage of secondary radiation. In addition, the apparatus of the invention requires less space than prior art apparatus using disks or cylinders.

DETAILED DESCRIPTION OF THE INVENTION

Figure 2:
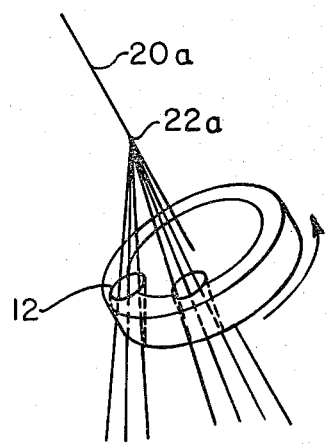
FIG. 2 illustrates another prior art device in which the angle and distance from the radiation source remain constant from the rotating disk having holes for passing radiation.

The object being radiographed may be any object which is at least partially transparent to high energy radiation and has a varying attenuation to radiation. "Attenuation," means that the intensity of radiation leaving the object is less than radiation entering the object due to absorbtion and scatter. The object may be inanimate or animate such as a human being. The high energy radiation is usually X-ray radiation but may be gamma radiation. The source of the radiation is usually an X-ray tube but may be a radioactive isotope. Radiation of energy lower than X-ray radiation is usually not used.

The radiation detection means may be any means having a detecting surface for detecting radiation. The detecting surface is that surface which is used to receive and detect radiation. The most usual radiation detection means (detector) is a luminescent screen; however, other detection means such as devices for generating electrical current in response to radiation may be used.

The flux pyramid is the pyramid formed by radiation from the source to the detecting surface in the absence of the object and shields. The flux pyramid may be of any shape defined by all straight lines from the circumference of the source to the detecting surface.

The radiation shield, in accordance with the present invention, has front and rear curvilinear shield surfaces. The curvilinear shield surfaces, including projected continuations thereof, are circularly symmetrical about a central axis and the surfaces, or their projected continuations, intersect the axis at at least one but not more than two apexes. "Projected continuation," means the mathematically continued surface in space as opposed to the portion of the curvilinear surface forming a part of the actual shield, i.e., "shield surface." The central axis of each of the front and rear surfaces is the same. The curvilinear surface, including projections, may be any curvilinear surface which is circularly symmetric about a central axis and which intersects the axis at at least one apex. Such surfaces include lateral conical surfaces, spherical surfaces, ellipsoidal surfaces, parabolic surfaces, hyperbolic surfaces, combinations thereof and surfaces which approach the curvature or shape of such surfaces. "Circularly symmetric" or "circularly symmetrical" is intended to include the central symmetry of shapes approaching precise circular symmetry such as shapes in the form of regular polygons having many sides, e.g. over 20 sides. When the curvilinear shield surface, and its projected continuations, is a closed surface such as a spherical or ellipsoidal surface, the central axis intersects the surface at two apexes; whereas, when the curvilinear shield surface and its projected continuations is an open infinite surface, such as a conical lateral surface, a parabolic or hyperbolic surface, the axis intersects the surface at only one apex.

The front surface of the shield faces the source. "Facing," when used in conjunction with the front surface facing the source, means that a straight line may be drawn from the source to any position on the front surface without passing through the rear surface. In addition, the front shield surface faces the central axis. "Facing," when used in conjunction with the front surface facing the central axis, means that a line drawn perpendicular to the surface at any point will intersect or nearly intersect the central axis. Nearly intersect means that such a perpendicular line will miss the central axis by a distance of less than two percent of the distance from the point to the central axis. At least a portion of the rear shield surface faces the detecting surface meaning that a straight line can be drawn from the detecting surface to the facing portion of the rear shield surface without passing through the front shield surface.

The shield is sufficiently dense and thick between the front and rear surfaces to absorb essentially all radiation from the source which strikes the shield. The shield is provided with a series of openings or holes, narrower than the object, passing through the shield from the front shield surface to the rear shield surface. The openings allow radiation to pass through the shield from the source to the detection means. The openings are in shapes and positions such that at least a portion of radiation in a straight line from the source toward the detection means passes through the openings in the shield to strike the detection means.

Means is provided for mounting the shield to make it movable about the central axis. In general, such means is one or more bearings secured to a central shaft having the central axis as its longitudinal axis. The mounting means is also used to align the central axis on a straight line from the source to the apexes of the surfaces so that all radiation passing from the source through the object must pass once through the utilized portion of the shield when the shield is in motion about the axis before the radiation stikes the detection means.

The apparatus further comprises means for moving the shield about the central axis. The means for moving the shield is generally a drive motor connected to and rotating the central shaft previously described. The motion about the central axis does not necessarily have to be a rotational motion but may be an oscillating motion. In such a case, the means for moving the shield about the central axis is frequently a cam mechanism connected to a drive means which is usually an electric motor. As previously discussed, the shield is provided with a series of openings or holes, narrower than the object, passing through the shield from the front to the rear surface. The openings allow radiation to pass through the shield from the source to the detection means. The openings are in shapes and positions such that at least a portion of radiation in a straight line from the source toward the detection means passes through the openings in the shield to strike the detection means.

The walls of the openings are approximately aligned with the angle of radiation in a straight line from the center of the source of the walls of the openings. "Approximately aligned," means aligned within ten degrees of the angle of incoming radiation. Since the distance of each of the holes from the source does not change, in accordance with the present invention, the alignment angle similarly does not change. As previously discussed, the side walls of the holes (if there are straight side walls) are essentially perpendicular to the curvilinear surface. Since such walls are designed to primarily permit the passage of primary radiation, secondary radiation, which usually strikes the shield at an angle different than the primary radiation, is substantially reduced.

The openings are frequently in the shape of sectors radiating outwardly from the apex of the surfaces. When the openings are slits in the shape of sectors, they desirably run from a location proximate the apex to a position proximate the external edge of the shield. The slits are desirably narrowest proximate the apex and widest proximate the external edge. The external edge is defined by the surface connecting the locus of points on the front and rear surfaces at positions farthest from the apex. The openings may also be spaces between grid elements of variable or constant thickness or may be any other desired shape.

Mostly desirably, the ratio of the sum of the widths of the openings to the sum of the widths of solid shield areas is essentially constant on the utilized portion of each shield as such widths are measured along the entire arc, within a curvilinear shield surface, of any circle perpendicular to the central axis having its center at the central axis.

A highly desirable curvilinear shield surface is a complete or truncated conical lateral surface. In such cases, the central axis is the central conical axis and the apex is the apex of the cone of the conical surface. In such cases, the shield is desirably mounted so that the bases of the cones are between the source and the apex of the conical surface. The apex angle of the cone of each of the conical surfaces is desirably such that at least one element of each of the conical lateral shield surfaces is projected upon the detecting surface by straight lines from the center of the source to the detecting surface to form a line within the detecting surface, which passes near the center of the detecting surface and is essentially parallel to the projected element. "Essentially parallel," means within ten degrees of parallel.

In such an arrangement, when the detection means is a planar surface, the maximum difference in distance between the distance from any part of the detecting surface to the source and the distance from any other part of the detecting surface to the source is minimized. Since the change in distance to the detecting surface from the source is minimized, the image distortion upon the detecting surface is similarly minimized. When the conical lateral surface is a truncated conical lateral surface, the apex is determined by projection of the truncated conical lateral surface.

If desired, a plurality of radiation shields may be used. For example, a second radiation shield may be provided between the source and the object. The utilized portion of the second radiation shield, in such a case, is smaller than but proportionally similar to the utilized portion of the first shield and is aligned with its central axis along the line from the center of the source to the apex of the front surface of the second shield such that primary radiation passing through an opening in the first shield toward the detecting surface, first passes through an essentially proportionally similarly shaped opening in the second shield when the object is absent and means is provided for moving the second shield at the same angular velocity as the first shield. "Proportionally similar," as used herein in comparing shields, means of the same relative overall proportions within a variation of less than about one percent including hole position but excluding hole size and shape. "Essentially proportionally similar," means of the same relative overall proportions within a variation of less than about five percent.

An even further radiation shield may be provided as a companion to the first radiation shield between the object and the first radiation shield. The companion radiation shield is smaller than but again the utilized portion is proportionally similar to the utilized portion of the first shield and again is aligned with its central axis along the line from the center of the source to the apex of its front surface such that radiation passing through an opening in the first shield, toward the detecting surface, first passes through an essentially proportionally similar opening in the companion shield and means is provided for moving the companion shield at the same angular velocity as the first shield.

When multiple shields are used, their curvilinear surfaces may be any curvilinear surface as previously described but the surfaces of the utilized portions of the shields should desirably be proportionally similar as between the shields. For example, all the surfaces of the shields may be conical lateral surfaces wherein the central axis is the central conical axis and the apex of each of the shields is the apex of the cone of the conical surfaces of each such shields.

The means for moving each shield may be a means for rotating the curvilinear surfaces about the central axis as previously described with respect to the first shield. The means for moving the shields may, for example, be a motor connected with a central shaft having the central axis as its longitudinal axis which shaft is connected to the centers of all such shields.

Desirably, the apparatus of the invention is designed so that radiation strikes the detection means in essentially uniform coverage of the detecting surface when the object is absent, when the source is uniform and when the shield is in motion for an integral number of complete cycles about the central axis. "Essentially uniform coverage," as used herein, means a variance of less than 10% over the surface of the detection means. In reality, radiation sources are not completely uniform nor are they located at a single point. However, designing the apparatus to maximize collection of primary radiation in a uniform pattern, while reducing collection of secondary radiation, based upon the assumption that the source is uniform and located at a single point (the actual source center), usually maximizes the collection of primary radiation, uniformity and reduction of collection of secondary radiation.

The invention further comprises the process for reducing detection of radiation scatter from an object by a radiation detecting surface which receives high energy radiation within a flux pyramid through the object from a radiation source. The process comprises interposing at least a first radiation shield, as previously described, between the object and the detector. The shield is aligned so that the central axis is on a straight line from the source to the apexes of the surfaces and so that all radiation passing from the source through the object must pass once through the shield when the shield is in motion about the axis, before the radiation strikes the detector. The process further comprises moving the shield about the central axis as previously described.

Figure 1:
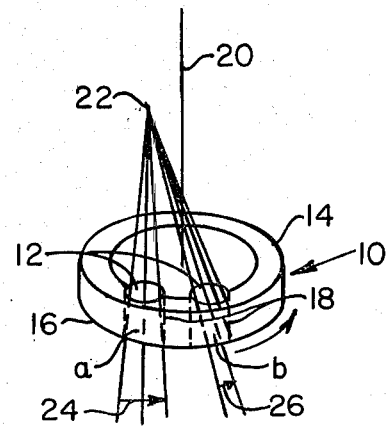
FIG. 1 illustrates a prior art device in which a rotating disk provided with holes was used as a shield.
Figure 3:
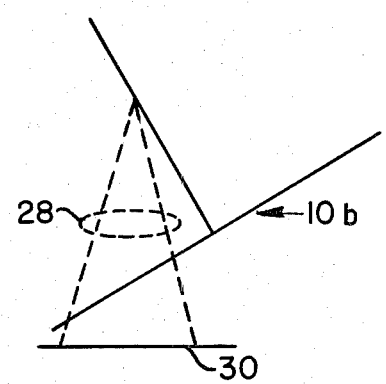
FIG. 3 is an illustration of the relationship of the radiation source disk and detecting device in the prior art FIG. 2 system.

To more fully and clearly understand the invention, reference may be had to the drawings. FIG. 1 shows a prior art rotating shield 10 in the form of a disk provided with holes 12 passing through the disk from front surface 14 to rear surface 16. The holes have side walls 18. The disk rotates about a central axis 20. A radiation source 22 is provided which is not located on axis 20. As can be seen from FIG. 1, a hole 12 at position A directly beneath source 22 and having perpendicular side walls will pass a substantial quantity of primary radiation as defined by arc 24. When hole 12 moves to position B, which is a further distance from source 22, the angle of radiation to side walls 18 changes thus the quantity of primary radiation passed through hole 12 is diminished as shown by arc 26. In the prior art, the problem of diminished radiation due to absorbtion by side walls of holes through the radiation shield due to changing radiation angle was substantially reduced by placing the source 22a on axis 20a as shown in FIG. 2. In this way, the distance from source 22a to holes 18a remained constant and thus the angle from source 22a to holes 18a also remained constant thus the quantity of radiation passing through holes 18a remained constant. Unfortunately, unless distorted oblique views of an object were desired, an arrangement as shown in FIG. 2 required that the object 28 be placed at an angle to disk 10b as shown in FIG. 3. The detector 30 was then placed parallel to object 28 to avoid angular distortion. As can best be seen in FIG. 3, placing the disk 10b at an angle to object 28 and detecting means 30 requires substantial space between the object and the detector and, in addition, requires substantial space for the disk itself.

Figure 4:
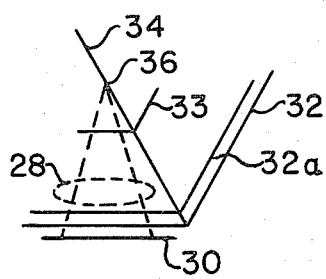
FIG. 4 is a schematic illustration of the invention device illustrating that the distance between the object and the detector is substantially reduced by the invention and also illustrating that a second radiation shield may be utilized.

In accordance with the present invention, as seen in FIG. 4, the distance required between the object 28 and the detector 30 is substantially reduced by using a shield 32 in accordance with the invention which has a curvilinear surface facing the rotational axis 34. In this way, a radiation source 36 can be placed on the rotational axis 34 so that any hole through shield 32 will always remain at a constant distance from source 36; yet, if desired, at least one element of shield 32 can remain parallel with both the plane of object 28 and detecting means 30. If desired, detector 30 can be itself in the form of a curvilinear surface similar to the surface of shield 32.

Figure 6:
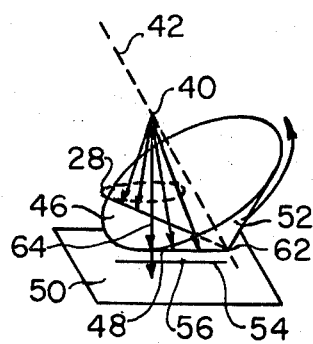
FIGS. 5, 6, 7 and 8 illustrate that the curvilinear shield surfaces are circularly symmetric about their central axis such that any line drawn perpendicular to the front curvilinear surface will intersect the axis.
Figure 5:
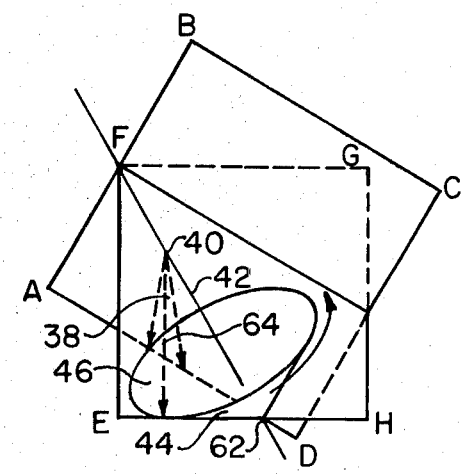
Figure 7:
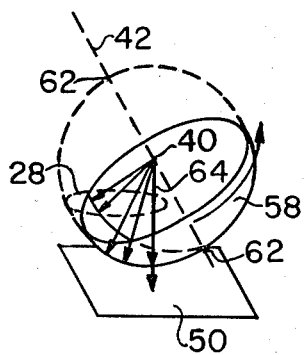
Figure 8:
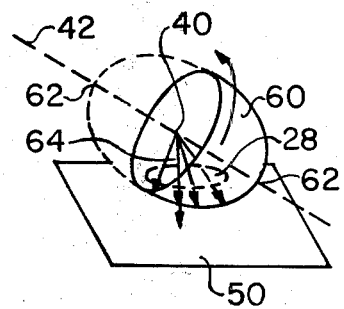

Stated in another way, as shown in FIG. 5, radiation 38 from a point source 40 located on central rotational axis 42 of shield 44 all lies in planes such as planes A, B, C, D and E, F, G, H which are perpendicular to front surface 46 of shield 44. Such planes all contain central axis 42. When the front curvilinear surface is a lateral conical surface 46 as shown in FIG. 5 and FIG. 6, desirably at least one element 48 of each of the conical lateral surfaces, i.e., front lateral surface 46 and rear lateral surface 52, is essentially parallel to a line within the detecting surface 50 which line 54 within the detecting surface 50 is located such that it passes near the center 56 of detecting surface 50. As seen in FIG. 7 and FIG. 8, the curvilinear surfaces may be in shapes other than conical surfaces. For example, FIG. 7 illustrates a curvilinear surface in the form of a spherical surface 58 and FIG. 8 illustrates a curvilinear surface in the form of an ellipsoidal surface 60. As best seen in FIGS. 5, 6, 7, and 8, the central axis 42 passes through apexes 62. Furthermore, as can be seen in FIGS. 5, 6, 7 and 8, the curvilinear shield surfaces, in conjunction with their projections, are circularly symmetric about central axis 42 such that any line drawn perpendicular to the front curvilinear surface will intersect axis 42. Such perpendicular lines may be represented by perpendicular radiation rays 64.

If desired, as shown in FIG. 4, additional curvilinear surfaces may be provided which are also circularly symmetrical about central axis 34. For example, a second radiation shield 33 is illustrated in FIG. 4 between the source 36 and the object 28. The second radiation shield 33 is smaller than but proportionally similar to the first shield 32 and is aligned with its central axis along the line from the center of the source to the apex of its front surface such that radiation passing through an opening in the first shield 32 passes through a proportionally similar opening in second shield 33 when object 28 is absent. FIG. 4 also shows a companion radiation shield 32a to first radiation shield 32 which is provided between object 28 and first radiation shield 32. Companion radiation shield 32a is smaller than but proportionally similar to first shield 32 and is aligned with its central axis 34 along the line from the center of the source to the apex of its front surface such that radiation passing through an opening in companion shield 32a passes through a proportionally similar opening in first shield 32.

Figure 9:
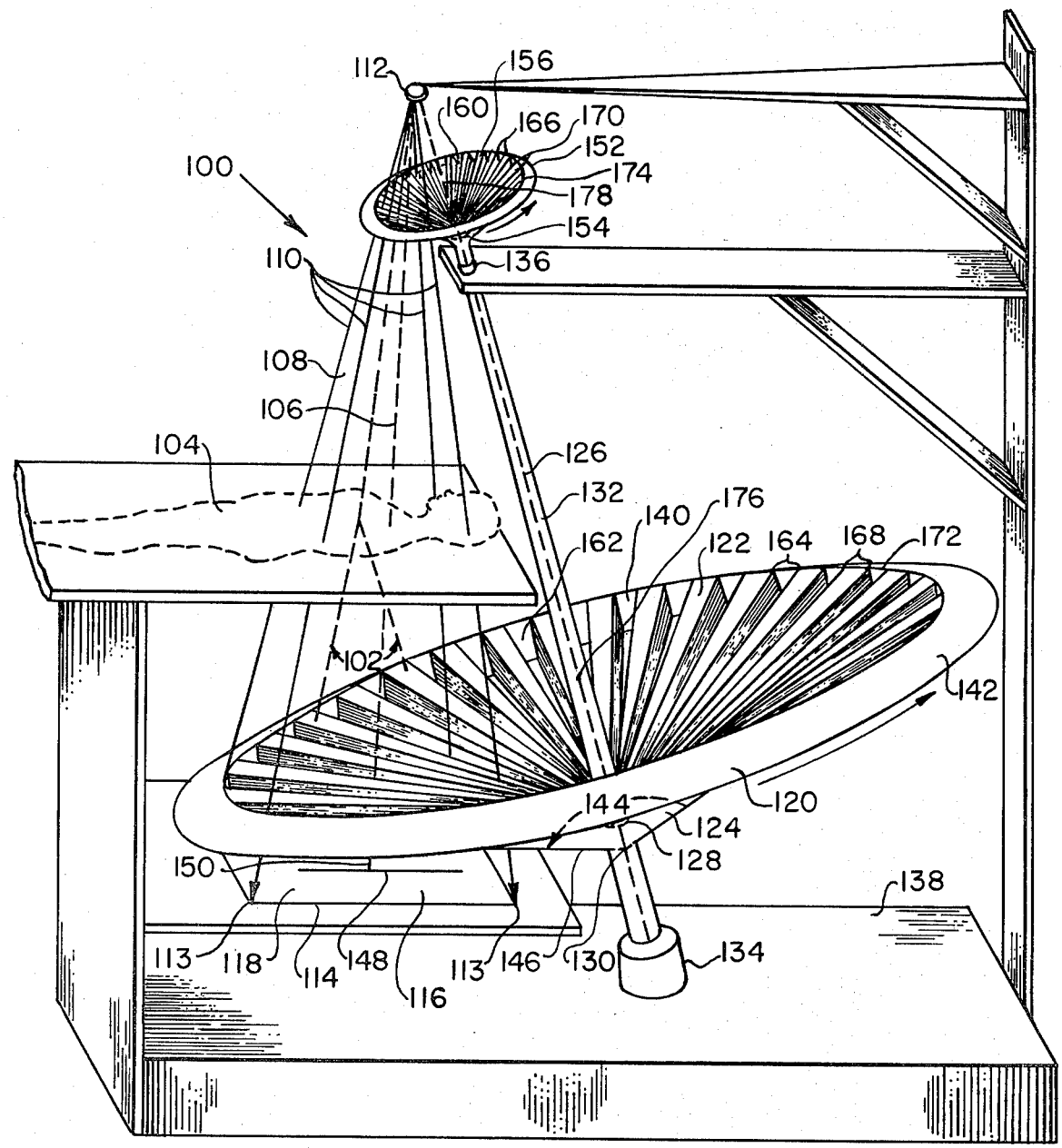
FIG. 9 is a view of apparatus in accordance with the invention that is utilized for X-ray imaging.

A more detailed drawing of an embodiment of the apparatus in accordance with the present invention is shown in FIG. 9. The apparatus 100 shown in FIG. 9 for reducing detection of radiation scatter 102 from an object 104 in which high energy radiation 106 within a flux pyramid 108 defined by rays 110 from a source 112 to the corners 113 of edge 114 of radiation detection means 116 having a detecting surface 118. The apparatus comprises a first radiation shield 120 having front and rear curvilinear surfaces 122 and 124 respectively in the form of conical lateral surfaces. Each of the conical lateral surfaces is circularly symmetrical about a central axis 126 and intersect central axis 126 at apexes 128 and 130 respectively. The central axis 126 of each of the surfaces is the same. Shield 120 is sufficiently thick and dense between the front and rear surfaces 122 and 124 to absorb essentially all radiation from source 112 which strikes shield 120. Front surface 122 faces the source 112 and faces the central axis 126. At least a portion of rear surface 124 faces detection means 116. Shield 120 is mounted upon central shaft 132 which has as its longitudinal axis central axis 126.

Central shaft 132 is in turn rotationally mounted within bearings 134 and 136 so that the central axis 126 is aligned on a straight line from the center of source 112 to apexes 128 and 130 of front and rear surfaces 122 and 124 so that all radiation within flux pyramid 108 passing from source 112 through object 104 must pass once through shield 120 when shield 120 is in motion about axis 126 before the radiation strikes detecting surface 118.

A means for moving the shield about the central axis is located within base 138 which moving means is connected with and rotates central shaft 132.

Shield 120 is provided with a series of openings 140 narrower than object 104 passing through shield 120 from front surface 122 to rear surface 124. The openings allow radiation 106 to pass through shield 120 from source 112 to detecting surface 118. The openings shown in FIG. 9 are slits running from a location proximate apexes 128 and 130 of surfaces 122 and 124 to a position proximate an external edge 142 of shield 120. The external edge 142 is defined by the surface connecting the locus of points on front and rear surfaces 122 and 124 at the positions farthest from apexes 128 and 130. "Proximate," means within 15% of the distance from the apex to the external edge. The slits 140 are narrowest proximate the apexes 128 and 130 and widest proximate external edge 142. The openings in the form of slits 140 are in shapes and positions such that at least a portion of radiation 106 in a straight line from the center of source 112 toward detecting surface 118 passes through openings 140 and shield 120 to strike detecting surface 118.

As seen in FIG. 9, the shield is mounted so that the bases of the cones of the conical surfaces are between source 112 and apexes 128 and 130 of the conical surfaces. The apex angle 144 of the cone of each of conical surfaces 122 and 124 is such that at least one element 146 is essentially parallel to a line 148 within the surface 118 of detection means 116 which line 148 within surface 118 is located such that it passes near the center 150 of the detecting surface 118. A second radiation shield 152 is provided between the source 112 and the object 104. Second radiation shield 152 is smaller than but proportionally similar to first shield 120. Second shield 152 is aligned with its central axis 126 along the line 126 from the center of the source 112 to the apex 154 of its front surface 156 such that radiation 106 passing through an opening 160 in second shield 152 passes through a proportionally similar opening 162 in first shield 120 when object 104 is absent. Second shield 152 is similarly connected to central shaft 132 and is moved about central axis 126 at the same angular velocity as first shield 120. In general, the openings in shields 120 and 152 are such that the ratio of the sum of the widths 164 and 166 of the openings 140 and 160 to the sum of the widths of solid shield areas 168 and 170 is essentially constant on each shield as such widths are measured along the entire arc, e.g., arcs 172 and 174, of any circle within a lateral conical surface of the shields which circle is perpendicular to central axis 126 and which circle has its center 176 and 178 respectively at the central axis 126.

What is claimed is:

1. An apparatus for reducing detection of radiation scatter from an object through which high energy radiation passes within a flux pyramid from a source to a radiation detection means having a detecting surface, said apparatus comprising:
   (a) at least one radiation shield having a utilized portion defined by front and rear curvilinear shield surfaces; each of said curvilinear shield surfaces, with projected continuations thereof, being circularly symmetrical about a central axis and said curvilinear shield surface, or a projected continuation thereof, intersecting said axis at at least one and not more than two apexes, the central axis of each of the front and rear surfaces being the same, said shield being sufficiently dense and thick between the front and rear shield surfaces to absorb essentially all radiation from the source which strikes the shield, the front surface facing said source and facing said central axis and at least a portion of the rear surface facing said detecting surface;
   (b) a means for mounting said shield, between the object and the detecting surface, to make it movable about the central axis, and to align the central axis on a straight line from the source to the apexes of the surfaces so that all radiation passing from the source through the object must pass once through said shield when the shield is in motion about said axis before striking the detecting surface; and
   (c) means for moving said shield about the central axis; said shield being provided with a series of openings, narrower than the object, passing through the shield from the front to the rear surface, which openings allow radiation to pass through the shield from the source to the detecting surface, said openings being in shapes and positions such that at least a portion of radiation in a straight line from said source toward said detecting surface passes through the openings in said shield to strike the detecting surface.

2. The apparatus of claim 1 wherein the curvilinear surfaces are conical lateral surfaces, the central axis is the central conical axis and the apex is the apex of the cone of the conical surface.

3. The apparatus of claim 2 wherein the shield is mounted so that bases of the cones are between the source and the apex of the conical surfaces.

4. The apparatus of claim 2 wherein the apex angle of the cone of each of said conical surfaces is such that at least one element of each of the conical lateral surfaces, projected upon the detecting surface by straight lines from the center of the source to the detecting surface, forms a line within the detecting surface which passes proximate the center of the detecting surface and is essentially parallel to the projected element.

5. The apparatus of claim 2 wherein the conical lateral surfaces are truncated conical lateral surfaces.

6. The apparatus of claim 1 wherein a second radiation shield is provided between the source and the object, the utilized portion of the second radiation shield being smaller than but proportionally similar to the utilized portion of said first shield, said second shield being aligned with its central axis along the line from the center of the source to the apex of its front surface such that primary radiation passing through an opening in said first shield, toward the detecting surface, first passes through an essentially proportionally similar opening in said second shield when the object is absent, and means is provided for moving the second shield at the same angular velocity as the first shield.

7. The apparatus of claim 1 or 6 wherein a companion radiation shield to the first radiation shield is provided between the object and the first radiation shield, the utilized surface of the companion radiation shield being smaller than but proportionally similar to the utilized surface of said first shield, said companion shield being aligned with its central axis along the line from the center of the source to the apex of its front surface such that radiation passing through an opening in said first shield, toward the detecting surface, first passes through an essentially proportionally similar opening in said companion shield, and means is provided for moving the companion shield at the same angular velocity as the first shield.

8. The apparatus of claim 6 wherein all the surfaces of the shields are conical lateral surfaces, the central axis is the central conical axis and the apexes are the apexes of the cones of the conical surfaces.

9. The apparatus of claim 7 wherein all the surfaces of the shields are conical lateral surfaces, the central axis is the central conical axis and the apexes are the apexes of the cones of the conical surfaces.

10. The apparatus of claim 1 wherein the means for moving said shield is a means for rotating the curvilinear surfaces about the central axis.

11. The apparatus of claim 1 wherein the means for moving said shield is a means for oscillating the curvilinear surfaces about the central axis.

12. The apparatus of claim 1 wherein the front and rear surfaces are parallel to each other.

13. The apparatus of claim 1 wherein said openings are slits in the shape of sectors running from a location proximate the apex to a position proximate an external edge of the shield, said slits being narrowest proximate the apex and widest near the external edge.

14. The apparatus of claim 1 wherein said openings are openings between grid members.

15. The apparatus of claim 1 wherein the ratio of the sum of the widths of the openings to the sum of the widths of solid shield areas is essentially constant on the utilized portion of each shield as such widths are measured along the entire arc, within a curvilinear shield surface, of any circle perpendicular to the central axis having its center at the central axis.

16. The apparatus of claim 1 wherein the radiation strikes the detection means in essentially uniform coverage of the detecting surface when the object is absent, when the source is uniform and when the shield is in motion for an integral number of complete cycles about the central axis.

17. The apparatus of claim 1 wherein the high energy radiation is X-ray radiation and the source is an X-ray tube.

18. The apparatus of claim 17 wherein the detection means is a luminescent screen.

19. A process for reducing detection of radiation scatter from an object by a radiation detection means having a detecting surface which receives high energy radiation within a flux pyramid through the object from a radiation source, which process comprises:
  (a) interposing at least a first radiation shield between the object and the detecting surface, said shield having front and rear curvilinear surfaces; each of said curvilinear surfaces, being circularly symmetrical about a central axis and said curvilinear surface or a projected continuation thereof intersecting said axis at at least one and not more than two apexes, the central axis of each of the front and rear surfaces being the same, said shield being sufficiently dense and thick between the front and rear surfaces to absorb essentially all radiation from the source which strikes the shield, the front surface facing the source and facing the central axis and at least a portion of the rear surface facing the detecting surface, said shield being provided with openings, narrower than the object, passing through the shield from the front to the rear surface;
  (b) aligning said shield so that the central axis is on a straight line from the source to the apexes of the surfaces and so that all radiation passing from the source through the object must pass once through the shield, when the shield, is in motion about the axis, before striking the detecting surface; and
  (c) moving the shield about the central axis.

20. The process of claim 19 wherein the ratio of the sum of the widths of the openings to the sum of the widths of the solid shield areas is essentially constant on the utilized portion of each shield, as such widths are measured along the entire arc, within a curvilinear shield surface of any circle, perpendicular to the central axis having its center at the central axis.

* * * * *